Figure 1A:
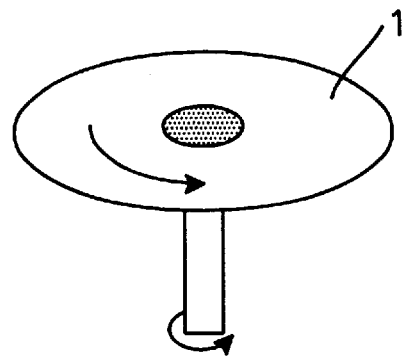

United States Patent [19]
Öhman

[11] Patent Number: 6,126,765
[45] Date of Patent: *Oct. 3, 2000

[54] METHOD OF PRODUCING MICROCHANNEL/MICROCAVITY STRUCTURES

[75] Inventor: Ove Öhman, Uppsala, Sweden

[73] Assignee: Pharmacia Biotech AB, Uppsala, Sweden

[*] Notice: This patent issued on a continued prosecution application filed under 37 CFR 1.53(d), and is subject to the twenty year patent term provisions of 35 U.S.C. 154(a)(2).

[21] Appl. No.: 08/564,217

[22] PCT Filed: Jun. 14, 1994

[86] PCT No.: PCT/SE94/00584

§ 371 Date: Dec. 15, 1995

§ 102(e) Date: Dec. 15, 1995

[87] PCT Pub. No.: WO94/29400

PCT Pub. Date: Dec. 22, 1994

[30] Foreign Application Priority Data

Jun. 15, 1993 [SE] Sweden .................................. 9302051

[51] Int. Cl.[7] ...................................................... B32B 31/16
[52] U.S. Cl. ........................... 156/74; 156/219; 156/292; 156/324.4; 204/600; 428/166
[58] Field of Search .................................. 156/74, 324.4, 156/219, 292; 428/166; 204/600

[56] References Cited

U.S. PATENT DOCUMENTS

| | | | |
|---|---|---|---|
| 3,475,867 | 11/1969 | Walsh | 156/74 |
| 3,759,773 | 9/1973 | Dwyer et al. | 156/280 |
| 4,957,582 | 9/1990 | Columbus | 156/292 |

FOREIGN PATENT DOCUMENTS 4128964  4/1993  Germany .

*Primary Examiner*—John J. Gallagher
*Attorney, Agent, or Firm*—Birch, Stewart, Kolasch & Birch, LLP

[57] ABSTRACT

In a method of forming a microchannel and/or microcavity structure by bonding together two elements (1, 2) having opposed plane surfaces of the same or different materials, one or both surfaces having open channels and/or cavities, bonding is effected by applying to one or both element surfaces (1, 2) a thin layer (3) of a solution of a material capable of fusing with and having a lower melting point than that of the material or materials of the two element surfaces (1, 2) in a solvent which substantially does not dissolve the element surface material or materials. The solvent is then removed, and the two elements (1, 2) are brought together and heated to a temperature where the dissolved material is caused to melt but not the element surface material or materials.

10 Claims, 1 Drawing Sheet

METHOD OF PRODUCING MICROCHANNEL/MICROCAVITY STRUCTURES

The present invention relates to the production of microchannel and microcavity systems, and more particularly to an improved method of bonding plane layers together in such production.

Microchannel or microcavity structures are used in inter alia chemical analytical techniques, such as electrophoresis and chromatography. In one type of such microfluidic structures, a channel and/or cavity system is defined between two plane material layers, the recesses which correspond to the channels and cavities, respectively, being formed in one or both of the opposed layer surfaces. The layers are usually bonded together by gluing. Alternatively, if the two layers consist of thermoplastic material, they may be fused together by the application of heat.

When very small channel dimensions are concerned, however, these conventional joining methods tend to deform the channel or cavity system to a great extent by partial clogging with glue or molten material.

The object of the present invention is to overcome this problem by providing a method which permits convenient bonding together of the material layers substantially without obstructing the channel or cavity system.

According to the invention, this is achieved by a method of forming a microchannel and/or microcavity structure by bonding together two elements (1, 2) having opposed plane surfaces of the same or different materials, one or both surfaces having open channels and/or cavities, characterized in that said bonding is effected by applying to one or both element surfaces (1, 2) a thin layer (3) of a solution of a material capable of fusing with and having a lower melting point than that of the material or materials of the two element surfaces (1, 2) in a solvent which substantially does not dissolve the element surface material or materials, removing the solvent, bringing the two elements (1, 2) together, and heating to a temperature where the dissolved material is caused to melt but not the element surface material or materials.

The invention is based on the concept that in order to bond together two planar element surfaces of the same or different materials, preferably thermoplastic, which surfaces when brought together define a channel and/or cavity system between them, there is applied to one or, preferably, both element surfaces a thin layer of another, preferably also thermoplastic, material dissolved in a solvent which does not dissolve the material of the two element surfaces. This dissolved material should, on one hand, be capable of being fused with the material(s) of the two surfaces on which it has been coated, and, on the other hand, melt at a lower temperature than the melting temperature of the element surface material or materials. After evaporation of the solvent, the two surfaces are brought together, e.g. by rolling, whereupon the assembly is heated to a temperature that melts the intermediate (preferably thermoplastic) material but not the material of the element surfaces for effecting joining of the two element surfaces.

The applied solution layer should, of course, have a very small thickness in relation to the width and depth of the channels and microcavities, respectively, which width and depth may be of the order of magnitude of 50 to 100 μm, for example.

When a thermoplastic material is used for the two material surfaces, this thermoplastic material is suitably closely related to the thermoplastic material responsible for the bonding of the channel/cavity structure. As an example of a suitable type of thermoplastic for the present purpose may be mentioned fluoroelastomers.

Suitable combinations of surface/bonding materials and solvents for practising the invention will readily be devised by the person skilled in the art guided by the present description.

Figure 1B:
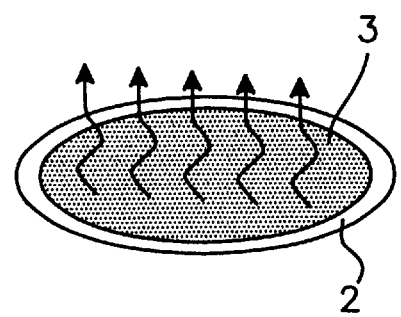
Figure 1C:
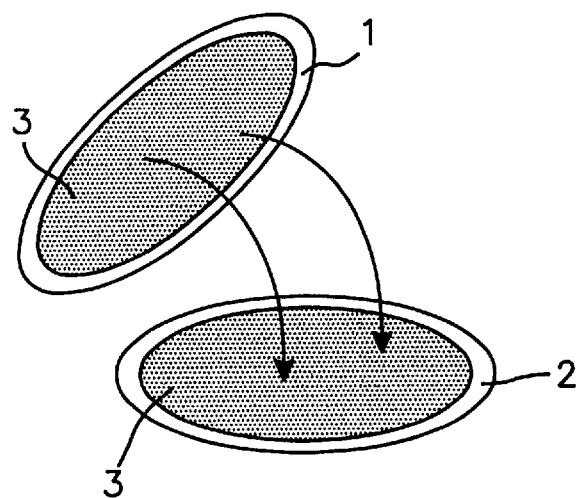
Figure 2:
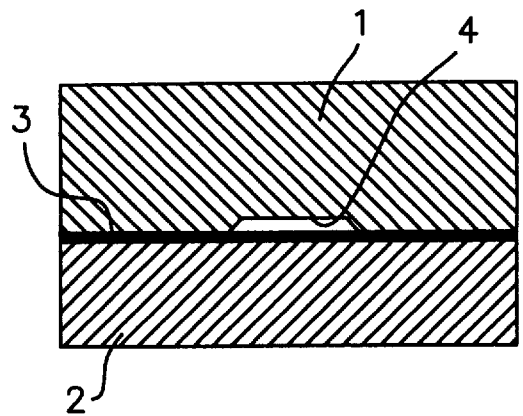

The carrying out of the process of the invention is illustrated schematically in the accompanying drawings, wherein FIGS. 1A to 1C show different substeps in the manufacture of a microfluidic structure, and FIG. 2 is a cross-section of the final product.

FIG. 1A shows a plate 1 provided with an open channel system (not shown), which plate together with an identical plate 2 without the channel system is intended to define a microchannel system between the two plates. For bonding the two plates together, which preferably are made of a thermoplastic material, e.g. a fluoroelastomer, a thin layer 3 of a, preferably closely related, thermoplastic material, e.g. a modified fluoroelastomer with a lower melting point, is first spun onto both plate surfaces. Then the solvent is baked off at an increased temperature (e.g. 135° C.), as is illustrated in FIG. 1B. The two plates treated in this way are then rolled together, as indicated in FIG. 1C, and are allowed to be bonded together for some time, e.g. 5 minutes. The completed microchannel structure is shown in FIG. 2. As may be seen from the latter figure, the two plates 1, 2, which are held together by the material layer 3, define a channel system 4 between them. The following specific Example, which describes the production of a microchannel structure, illustrates the method of the invention further.

EXAMPLE

A polymer structure with closed straight channels having a height of 50 μm, a width of 250 μm and a length of about 80 mm was produced in the following manner.

A silicon mould having a surface relief structure corresponding to the desired channel geometry was manufactured in per se known manner. Thus, the surface of a silicon plate was first oxidized at about 1100° C. to form an oxide layer of 8000 Å thickness. After washing, dehydration in an oven and priming with hexamethylsilane, a photoresist layer was spun onto the oxide layer and was stabilized by baking in an oven. A mask corresponding to the desired channel pattern was then placed on the plate surface, and the surface parts not covered by the mask were exposed to light. The exposed photoresist parts were then removed by developing solution to bare the oxide layer, and the remaining photoresist was hard-baked. The bared oxide was then etched with hydrofluoric acid/ammonium fluoride to expose the silicon (the backside of the plate being protected by resistant tape), whereupon the photoresist mask was removed by acetone. The oxide-free silicon surfaces were then etched with potassium hydroxide solution for a sufficient time to produce the desired etch depth.

The resulting surface exhibited the desired channel pattern.

The silicon mould obtained was then pressed against a 2 mm thick film of Hostaflon TFB 7100 (refractive index about 1.36) at about 160° C. and 20 kp/cm$^2$. (Hostaflon is a thermoplastic fluoroelastomer sold by Hoechst AG, Germany). The resulting channel structure was bonded to a base layer in the form of a plane plate of the same material by spinning a thin layer of Hostaflon TFB X-7200 (having a lower melting point than that of Hostaflon TFB 7100) dissolved in propylmethylketone onto the base layer and the channel structure, which were then allowed to dry at 130° C. for 10 minutes. The channel structure and the base layer were then immediately rolled together, and the obtained sandwich was baked at about 140° C. for 10 minutes. The polymer structure produced in this way exhibited intact closed channels.

The invention is, of course, not restricted to the embodiment described above and specifically shown in the drawing, but many modifications and changes may be made within the scope of the general inventive concept as it is stated in the following claims.

I claim:

1. A method of forming a microchannel and/or microcavity structure, comprising the steps of:

providing a plane mould surface having an etching-derived relief structure corresponding to a desired microchannel and/or microcavity geometry;

moulding a first element against said mould surface such that said first element obtains a plane surface with open microchannels and/or microcavities having a depth of about 100 μm or less;

providing a second element having a plane surface of the same or different material than said first element;

applying to the plane surface of one or both of said first and second elements a thin layer of a solution of a dissolved thermoplastic material capable of fusing with and having a lower melting point than that of the material or materials of the two element surfaces in a solvent which substantially does not dissolve the element surface material or materials;

removing the solvent;

bringing said plane surfaces of said first and second elements together to define a closed microchannel and/or microcavity system between them; and heating to a temperature where the dissolved thermoplastic material is caused to melt but not the element surface material or materials to bond said first and second elements together, whereby the first and second elements are bonded together substantially without obstructing the microchannel and/or microcavity system.

2. The method according to claim 1, characterized in that the two elements that are to be bonded together are of the same material.

3. The method according to claim 1, characterized in that the material of the two elements is thermoplastic.

4. The method according to claim 3, characterized in that the material of the two elements and the dissolved material are of substantially the same type.

5. The method according to claim 4, characterized in that the materials of the two elements and the dissolved material are fluoroelastomers.

6. The method of claim 1, wherein said first element contains a microchannel and wherein the height of said microchannel is about 50 μm.

7. The method of claim 1, wherein said first element contains a microchannel and wherein the width of said microchannel is about 250 μm.

8. The method of claim 1, wherein the width and depth of said microchannels and/or microcavities are on the order of magnitude of 50 to 100 μm.

9. The method of claim 1, wherein said solution of dissolved thermoplastic material is applied to said surface or surfaces by spinning.

10. The method of claim 1, wherein said first element is thermoplastic and is moulded by heating the element and pressing the element against the mould surface.

* * * * *